(12) United States Patent
Srivastava et al.

(10) Patent No.: US 6,541,514 B2
(45) Date of Patent: Apr. 1, 2003

(54) PROCESS FOR THE MANUFACTURE OF 117SN DIETHYLENETRIAMINEPENTAACETIC ACIDS

(75) Inventors: Suresh C. Srivastava, Setauket, NY (US); Zizhong Li, Upton, NY (US); George Meinken, Middle Island, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 28 days.

(21) Appl. No.: 09/847,617

(22) Filed: May 2, 2001

(65) Prior Publication Data

US 2002/0187975 A1 Dec. 12, 2002

(51) Int. Cl.$^7$ .......................... A61K 31/32; C07F 7/22; A61M 36/14
(52) U.S. Cl. ................. 514/493; 424/1.65; 534/10; 556/105; 600/1; 600/3
(58) Field of Search .................. 600/1, 3; 534/10; 514/493; 424/1.65; 556/105

(56) References Cited

U.S. PATENT DOCUMENTS

| | | | |
|---|---|---|---|
| 4,533,541 A | 8/1985 | Srivastava et al. | 424/1.1 |
| 5,853,695 A | 12/1998 | Srivastava et al. | 424/1.65 |
| 6,004,532 A | 12/1999 | Srivastava et al. | 424/1.65 |

FOREIGN PATENT DOCUMENTS

| | | |
|---|---|---|
| WO | WP 95/29706 | 11/1995 |

OTHER PUBLICATIONS

Atkins, et al. "Biodistribution of Sn–117m(4+) DTPA for Palliative Therapy of Painful Osseous Metastases", *Radiology*, 186, 279–283 (1993).
Atkins, et al. "Tin–117m(4+)–DTPA for Palliation of Pain from Osseous Metastases: A Pilot Study", *Nucl. Med.*, 36, 725–729 (1995).
Krishnamurthy, et al., "Tin–117m(4+)DTPA: Pharmacokinetics and Imaging Characteristics in Patients with Metastatic Bone Pain", *J. Nucl. Med.*, 38, 230–237 (1997).
Srivastava, et al., "Treatment of Metastatic Bone Pain with Tin–117m Stannic Diethylenetriaminepentaacetic Acid: A Phase I/II Clinical Study", *Clin. Cancer Res.* 4, 61–68 (1998).

*Primary Examiner*—Porfirio Nazario-Gonzalez
(74) *Attorney, Agent, or Firm*—Margaret C. Bogosian

(57) ABSTRACT

Novel methods are provided for the manufacture of $^{117m}$Sn (Sn$^{4+}$) DTPA. The method allows the use of DTPA, a toxic chelating agent, in an approximately 1:1 ratio to $^{117m}$Sn (Sn$^{4+}$) via either aqueous conditions, or using various organic solvents, such as methylene chloride. A pharmaceutical composition manufactured by the novel method is also provided, as well as methods for treatment of bone tumors and pain associated with bone cancer using the pharmaceutical composition of the invention.

25 Claims, 2 Drawing Sheets

Ortep View of HSn(DTPA)•$3H_2O$

Carbon-13 NMR Spectrum in D$_2$O

PROCESS FOR THE MANUFACTURE OF 117SN DIETHYLENETRIAMINEPENTAACETIC ACIDS

This invention was made with Government support under contract number DE-AC02-98CH10886, awarded by the U.S. Department of Energy. The Government has certain rights in the invention.

BACKGROUND OF THE INVENTION

Bone metastases are the most common cause of cancer pain, and primary bone cancers may also cause severe chronic pain. Approximately 75–80% of patients with prostate, breast, and lung cancer develop osseous metastases which cause bone pain during the late stages of their illness. Clinical management of cancer-related bone pain through palliation is necessary to improve the quality of life of terminal cancer patients.

A number of options are currently available for clinical management of bone pain. Nonsteroidal anti-inflammatory agents, opioids, hormones, and cytotoxic chemotherapy are used in the initial stages of bone metastasis, and external beam radiation can be applied locally when bone pain occurs at a single site. As the patient's skeletal tumor burden increases, pain can increase and become multifocal, tending to move from one site to another. Hemibody external beam radiation can afford rapid pain relief for disseminated skeletal tumors. However, such extensive exposure to radiation may affect noncancerous rapidly dividing tissues in the gastrointestinal tract or bone marrow, and morbidity may result from hemibody radiotherapy for bone pain palliation.

Radiation emitted by intravenously administered radionuclides may also be used to treat bone pain palliation. A number of bone-seeking radioisotopes have been studied for their ability to palliate bone pain. For example, $^{32}P$, which emits a 1.7 MeV β particle and has a half-life of 14.3 days, exhibits a 3- to 5-fold increase in uptake in bone around osseous metastases as compared to normal bone. The uptake of $^{32}P$ into bone lesions can be increased by pretreatment with androgen, and patients thus treated frequently experienced pain relief within five to fourteen days of $^{32}P$ orthophosphate administration, with response duration of two to four months. However, bone marrow receives a disproportionately high dose of $^{32}P$ from the surrounding inorganic bone matrix and from the cellular component of the bone marrow space, resulting in myelosuppression as a side effect. Pancytopenia resulting from myelosuppression by $^{32}P$, though reversible, may necessitate transfusions. $^{32}P$ orthophosphate is not currently used for palliation of metastatic bone pain.

$^{153}Sm$ emits an 0.81 MeV β particle, with a half-life of 46.3 hours. The stable $^{153}Sm$ ethylenediaminetetramethylenephosphonate (EDTMP) complex has received FDA approval. Patients report clinical benefit within two weeks of $^{153}Sm$-EDTMP treatment, frequently within 48 hours of treatment, and pain relief may last from four to forty weeks. Reversible myelosuppression also results from bone pain palliation treatment with $^{153}Sm$-EDTMP. In addition, at the applied therapeutic doses (35 to 210 mCi) large amounts of radioactivity can be excreted in the patient's urine, creating contamination risks and potentially causing radiation cystitis.

$^{186}Re$ emits a 1.07 MeV β particle and a 137 keV, 9% abundance γ photon, having a half-life of 89.3 hours. $^{186}Re$ forms a stable complex with hydroxyethylidine diphosphonate (HEDP) which rapidly accumulates in osteoblastic metastases. Symptom relief occurs for 40–65% of patients within two weeks, and frequently within 24–48 hours. $^{186}Re$-HEDP causes reversible myelosuppression, and therapeutic doses of $^{186}Re$-HEDP (30 to 70 mCi) also create contamination and radiation cystitis risks. Phase III clinical trials of $^{186}Re$-HEDP have been completed.

$^{89}Sr$ emits a 1.46 MeV β particle and has a half-life of 50.5 days. The biological half-life of $^{89}Sr$ exceeds 50 days in osteoblastic metastases, as compared to 14 days in normal bone. Bone pain relief occurs in 60 to 80% of patients, with onset two to four weeks after injection, though some patients may not experience relief for as much as ten weeks after treatment. The average duration of relief from $^{89}Sr$ treatment is from three to six months. Treatment with $^{89}Sr$ delays development of new bone pain in pre-existing, but clinically silent metastases. Four weeks after therapy, $^{89}Sr$ treatment typically causes a 30% decrease in platelet count, which recovers slowly over 12 weeks. Toxicity from $^{89}Sr$ treatment is cumulative, resulting from the total absorbed dose of radiation delivered to the bone marrow and from replacement of marrow by tumor as disease advances. In 1993, the FDA approved an adult dosage of 4 mCi of $^{89}SrCl_2$ for bone pain palliation.

Although pain relief is believed to occur independently from radiation-induced tumor cell killing, administration of bone pain-palliating doses of $^{153}Sm$ and $^{186}Re$ results in transient changes in levels of certain biochemical markers related to cancer progression. When administered with low doses of cisplatin, $^{89}Sr$ also demonstrates reductions in tumor markers. This observation has led to the suggestion that administration of higher doses of these nuclides might result in a tumoricidal effect. However, no anti-tumor effect or improvement in survival has been demonstrated to result from administration of $^{153}Sm$, $^{186}Re$, or $^{89}Sr$, and the ability to increase dosages of these nuclides is limited by their myelosuppressive effects.

$^{117m}Sn$ emits low energy conversion electrons (0.13 and 0.16 MeV) and a 159 keV photon, having a half-life of 14.0 days. $^{117m}Sn$ ($Sn^{4+}$) diethylenetriaminepentaacetic acid (DTPA) exhibits higher bone uptake and retention than $^{32}P$ orthophosphate, $^{153}Sm$-EDTMP, $^{186}Re$-HEDP, and $^{89}SrCl_2$. Because of this, therapeutic doses of $^{117m}Sn$ ($Sn^{4+}$) DTPA are lower than those of $^{153}Sm$-EDTMP and $^{186}Re$-HEDP, resulting in less risk of contamination and radiation cystitis. The lower energies of the conversion electrons emitted by $^{117m}Sn$ result in less radiation exposure to the bone marrow and fewer hematologic side effects than are observed with $^{153}Sm$-EDTMP, $^{186}Re$-HEDP, and $^{89}SrCl_2$. The photon emitted by $^{117m}Sn$ allows imaging and quantification of the isotope in normal and metastatic bone. $^{117m}Sn(Sn^{4+})$ is particularly suitable for the dose escalation necessary to effect cell killing in osseous tumors, since the myelosuppression which limits the benefits of the anti-tumor effects of $^{153}Sm$, $^{186}Re$, and $^{89}Sr$ is not a limiting factor for $^{117m}Sn$ ($Sn^{4+}$).

Atkins, et al., Radiology (1993) 186, 279–283, discloses biodistribution of low doses of $^{117m}Sn$ ($Sn^{4+}$) DTPA administered to humans. Atkins, et al. (1995) J. Nucl. Med. 36, 725–729 reports a Phase II pilot study which demonstrates palliation of bone pain resulting from $^{117m}Sn$ ($Sn^{4+}$) DTPA treatment. A Phase II study of $^{117m}Sn$ ($Sn^{4+}$) DTPA as a bone pain palliation agent is reported in Krishnamurthy, et al. (1997) J Nucl. Med. 38, 230–237. A dose escalation study of 47 patients treated with $^{117m}Sn$ (Sn4+) DTPA for bone pain palliation is reported in Srivastava, et al. (1998) Clin. Cancer Res. 4, 61–68. All of the $^{117m}Sn$ ($Sn^{4+}$) DTPA formulations used in these studies contained a 20-fold molar excess of DTPA over $^{117m}$Sn (Sn$^{4+}$) and an amount of CaCl$_2$ corresponding to 80% of the molar amount of DTPA. The CaCl$_2$ was administered with the $^{117m}$sn (Sn$^{4+}$) DTPA to counteract any potential effect of uncomplexed DTPA on bone or blood calcium levels.

U.S. Pat. No. 4,533,541 discloses preparation of $^{117m}$Sn (Sn$^{4+}$) chelates capable of localizing to bone after intravenous injection, which were used for diagnostic purposes. The chelating agents disclosed in U.S. Pat. No. 4,553,541 include DTPA, which was formulated in significant molar excess (8–40-fold) over the concentration of $^{117m}$Sn (Sn$^{4+}$) (i.e., the concentration of total tin) in the radiopharmaceutical composition.

WO 95/29706 discloses $^{117m}$Sn (Sn$^{4+}$) DTPA compositions for bone pain palliation and bone cancer therapy, which employ a molar excess of DTPA over $^{117m}$Sn (Sn$^{4+}$). WO 95/29706 demonstrates dose-dependent relief of bone pain in humans after administration of $^{117m}$Sn (Sn$^{4+}$) DTPA, with particular efficacy at doses of about 9 to about 25 mCi per 70 kg body weight. None of the $^{117m}$Sn (Sn$^{4+}$) DTPA compositions used in WO 95/29706 exhibited bone marrow toxicity, thus providing a significant advantage over the known agents. In a preferred embodiment, CaCl$_2$ was included with the $^{117m}$Sn (Sn$^{4+}$) DTPA compositions of WO 95/29706, to inhibit or retard possible hypocalcemic effects of the unchelated tin chelating agent DTPA.

U.S. Pat. No. 6,004,532 discloses a process for the manufacture of $^{117m}$Sn(Sn$^{4+}$)DTPA which includes the reaction of DTPA at a molar concentration from about eight to about twenty times the molar concentration of $^{117m}$Sn(Sn$^{4+}$) to form a $^{117m}$Sn(Sn$^{4+}$)DTPA complex and then removing the excess DTPA by chromatographic means. Because of the toxicity of the DTPA, this process requires the additional step of the removal of the excess DTPA.

SUMMARY

The present invention provides a method of making a pharmaceutical composition of $^{117m}$Sn(Sn$^{4+}$)DTPA. This first method provided utilizes an aqueous solvent and is therefore termed "aqueous reaction" herein. The method includes the steps:

a) dissolving metallic $^{117m}$Sn in a concentrated acid suspended in an aqueous medium to form a $^{117m}$SnCl$_2$ solution;

b) adding the DTPA to $^{117m}$SnCl$_2$ solution in a molar concentration ratio of between about 1.0 to about 3.0 DTPA to $^{117m}$SnCl$_2$;

c) allowing the $^{117m}$SnCl$_2$ to react with the DTPA to form a $^{117m}$Sn(Sn$^{2+}$)DTPA complex;

d) oxidizing the $^{117m}$Sn(Sn$^{2+}$)DTPA to form a composition comprising $^{117m}$Sn(Sn$^{4+}$)DTPA; and e) removing the concentrated acid and water from the solution to form to form a resulting solid composition comprising $^{117m}$Sn(Sn$^{4+}$)DTPA complex with a molar ratio of DTPA to $^{117m}$Sn(Sn$^{4+}$) of about 1.0 to about 3.0. In a preferred embodiment, the resulting composition comprises $^{117m}$Sn(Sn4+)DTPA with a molar ratio of DPTA to $^{117m}$Sn(Sn$^{4+}$) of about 1 to about 1.2.

In a separate embodiment, another method of making a pharmaceutical composition of $^{117m}$Sn(Sn$^{4+}$) DTPA is provided. This method utilizes organic solvents and therefore is termed the "organic reaction" herein. This method the steps:

a) dissolving metallic $^{117}$Sn in a concentrated acid suspended in an aqueous medium to form a $^{117m}$SnCl$_2$ solution under an inert atmosphere;

b) adding DTPA to the $^{117m}$SnCl$_2$ solution in a molar concentration ratio of between about 1.0 to about 3.0 DTPA to $^{117m}$SnCl$_2$ in an inert atmosphere;

c) removing the concentrated acid and water from the solution to form a solid residue comprising unchelated $^{117m}$SnCl$_2$ and DTPA;

d) dissolving the solid residue in an organic solvent to form an organic mixture, e) allowing the organic mixture to react sufficient to allow the formation of a $^{117m}$Sn(Sn$^{2+}$)DTPA complex;

f) oxidizing the $^{117m}$Sn(Sn$^{2+}$)DTPA to form a resulting composition comprising $^{117m}$Sn(Sn$^{4+}$)DTPA with a molar ratio of DTPA to $^{117m}$Sn(Sn$^{4+}$) of about 1.0 to about 3.0.

In a preferred embodiment, the resulting composition comprises $^{117m}$Sn(Sn$^{4+}$)DTPA with a molar ratio of DPTA to $^{117m}$Sn(Sn$^{4+}$) of about 1 to about 1.2.

The pharmaceutical composition manufactured by each of the aqueous reaction and organic reaction is also provided. These pharmaceuticals can be utilized in a method of treating primary or metastatic tumor in skeletal bone of a mammal. The method includes administering to the mammal a therapeutically effective amount of the pharmaceutical manufactured by either the aqueous or organic reactions.

A method of treating bone pain is also provided herein. This method also includes administering to a mammal a bone palliating amount of a pharmaceutical manufactured by either the aqueous or organic reaction method.

The method of the invention provides the benefit of a one-step reaction which, due to the ease of formulation, will result in minimizing personnel exposure, reduce waste, provide greater contamination control, and greatly simplify the eventual commercial production of $^{117m}$Sn(Sn$^{4+}$)DTPA. Unlike previous methods, the purification step to remove excess DTPA is not necessary in the method of the invention because DTPA and $^{117m}$Sn(Sn$^{4+}$) are reacted at an approximately 1:1 ratio. The $^{117m}$Sn(Sn$^{4+}$) DTPA produced by the method of the invention possesses the same chemical (shelf life and stability) and biological (biodistribution in mice) properties, compared to the current 20:1 $^{117m}$Sn(Sn$^{4+}$)DTPA formulation.

Because the method of the invention can provide a composition having a lower ratio of DTPA to $^{117m}$Sn(Sn$^{4+}$) (i.e. less than 3:1), the composition resulting from the method of the invention contains less of the toxic unchelated DTPA. This reduced toxicity allows more of the composition to be administered which, in turn, also permits the use of low specific activity $^{117m}$Sn. Therefore, the radiopharmaceutical produced by the method of the invention can be utilized in the higher quantities to not only provide pain palliation in bone cancer patients, but also be used for bone cancer treatment.

DETAILED DESCRIPTION OF INVENTION

Figure 1:
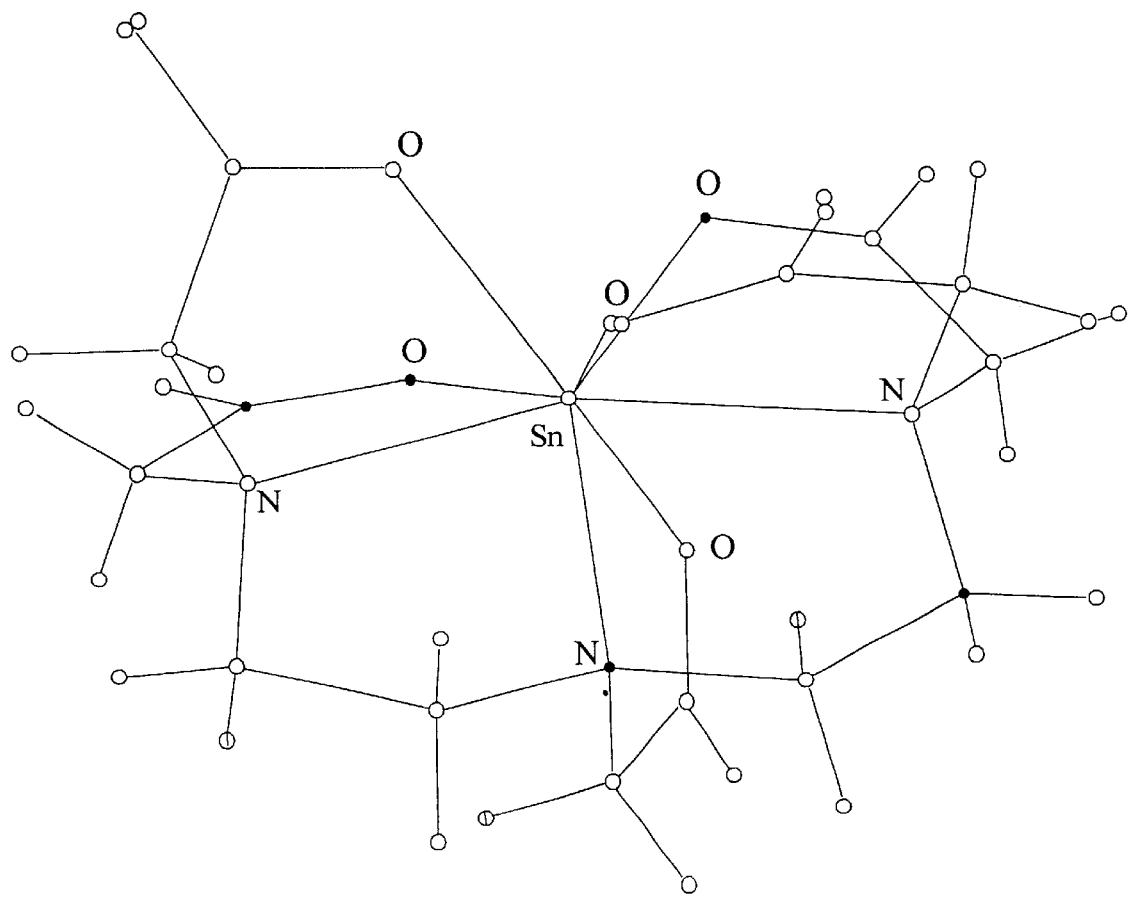
FIG. 1 depicts the structure of the Sn(Sn$^{4+}$) DTPA of the invention analyzed by x-ray crystallography.

The method of the invention provides a radiopharmaceutical composition. More specifically, the method of the invention provides a $^{117m}$Sn(Sn$^{4+}$)DTPA composition having a low DTPA to $^{117m}$Sn(Sn$^{4+}$) ratio, i.e. less that 3:1, preferably about 1:1.

The $^{117m}$Sn can be obtained by any suitable source. High specific activity $^{117m}$Sn is preferred; however, the ability to use low specific activity $^{117m}$Sn in the pharmaceutical compositions of the present invention provides greater flexibility in manufacturing for several reasons. First, there are a larger number of low flux reactors and cyclotrons than high flux reactors. Second, nuclear reactions other than the presently preferred $^{117}$Sn(n,n'$_\gamma$)$^{117m}$Sn reaction may be employed to produce $^{117m}$Sn.

In one embodiment, the $^{117m}$Sn has a specific activity from about 0.1 mCi/mg to about 80 Ci/mg. In another embodiment, the $^{117m}$Sn has a specific activity from about 2 mCi/mg to about 80 Ci/mg. In yet another embodiment, the $^{117m}$Sn has a specific activity from about 2 mCi/mg to about 20 mCi/mg.

$^{117m}$Sn may be produced in any way for use in the present invention, for example using any of the methods discussed in Mausner, et al. (1992) Appl. Radiat Isot. 43, 1117–1122. As disclosed in WO 95/29706, enriched $^{117}$Sn may be obtained as an oxide or as the metal, for example, from Oak Ridge National Laboratory, Oak Ridge, Tenn. The former may be converted to the metal by reduction at 600° C. in a hydrogen flow for 2.5 hours. A target may be prepared by sealing 4 to 100 mg of the $^{117}$Sn metal in a quartz ampule. To produce $^{117m}$Sn, the target is irradiated in a high flux reactor for periods up to 4 weeks. When $^{117m}$Sn is produced in a low flux reactor, the $^{117}$Sn target may be irradiated for periods of more than four weeks. $^{117m}$Sn may also be produced in a cyclotron, for example, by the $^{nat}$Sb(p,an/a3n)$^{117m}$Sn reaction or by the $^{114}$Cd(a,n)$^{117m}$Sn reaction.

The process of the invention can proceed in either aqueous or organic medium. The reaction in aqueous medium is preferred.

In the aqueous reaction, metallic $^{117}$Sn or $^{117m}$Sn produced as described above is dissolved in a minimal amount, about 1.0 to 5.0 ml, preferably 1.0 ml, of a concentrated acid, such as hydrochloric acid, in an aqueous medium to form a solution of $^{117m}$SnCl$_2$. Concentrated acid can be, for example, between 6–12 N. Amounts of tin between 1.0 to 100 mg can be dissolved in up to 5.0 ml, preferably 1.0 ml, of the concentrated acid, with heating.

DTPA, preferably solid DTPA, is then added to the solution of $^{117m}$SnCl$_2$. The DTPA is added to the $^{117m}$SnCl$_2$ solution in a molar ratio of about 1 to about 3, preferably between about 1.0 to about 1.2, DTPA to $^{117m}$SnCl$_2$. The $^{117m}$SnCl$_2$ is then permitted to react with the DTPA to form $^{117m}$Sn(Sn$^{2+}$)DTPA.

The solution is then permitted to oxidize to allow the oxidation of $^{117m}$Sn(Sn$^{2+}$)DTPA to $^{117m}$Sn(Sn$^{4+}$)DTPA. This oxidation step can be performed by simple exposure of the solution to open air, e.g. three to 12 hours, or the addition of hydrogen peroxide, as is known in the art. The concentrated acid and water are then removed by conventional means, such as under vacuum, to produce a solid residue.

In a separate embodiment, the reaction can be carried out in an organic solvent. For this organic reaction, $^{117m}$Sn is dissolved in concentrated acid to form a $^{117m}$SnCl$_2$ solution as described above. The $^{117m}$Sn is dissolved in the concentrated acid under an inert atmosphere, such as Ar or N$_2$.

DTPA is then added to the $^{117m}$SnCl$_2$ solution as discussed above. However, because this step also occurs in an inert atmosphere, a substantial quantity of the $^{117m}$SnCl$_2$ and DTPA may remain uncomplexed. At this stage, contrary to the aqueous method, the $^{117m}$SnCl$_2$/DTPA mixture is not oxidized. The concentrated acid and water are removed by conventional means to produce $^{117m}$Sn(Sn$^{2+}$) and DTPA residue, without previous oxidation.

The solid $^{117m}$SnCl$_2$/DTPA residue is then dissolved in an organic solvent. Examples of such organic solvents include methylene chloride, ethanol, and others. Methylene chloride is preferred. The organic mixture is then permitted to react for a sufficient amount of time, e.g. 12 hours, to enable $^{117m}$Sn(Sn$^{2+}$) DTPA complexation. The organic mixture is then evacuated to dryness by conventional means to form a resulting solid.

The resulting solid is then taken up in water, and the mixture oxidized from $^{117m}$Sn(Sn$^{2+}$) DTPA to $^{117m}$Sn(Sn$^{4+}$) DTPA. The oxidation of tin from stannous to stannic generally proceeds quite satisfactorily upon letting the mixture sit under air for about 3 hours to 12 hours. Also, an oxidizing agent, such as hydrogen peroxide, may be added to oxidize the $^{117m}$Sn (Sn$^{2+}$) to $^{117m}$Sn (Sn$^{4+}$). Oxidation is allowed to proceed for a suitable time, for example, for ten to fifteen minutes when hydrogen peroxide is employed.

The resulting solid, obtained either using aqueous or the non-aqueous reactions as set forth above, dissolved in water, may optionally be heated, for example in a boiling water bath, to facilitate complexation. The temperature should be sufficient to facilitate complexation, without destroying the desired product. Examples of such temperature ranges are as achieved in a boiling water bath preferably between about 90° C to about 100° C. If a heating step is performed, the $^{117m}$Sn (Sn$^{2+}$) DTPA solution is cooled to approximately room temperature. The pH of the solution containing $^{117m}$Sn (Sn$^{4+}$) DTPA is adjusted to between about 3 to about 5, preferably between about 4 to about 4.5. The solution is then reheated and cooled.

The resulting composition has a molar ratio of DTPA to $^{117m}$Sn(Sn$^{4+}$) of between about 3.0 to about 1.0. That is, in the pharmaceutical composition of the invention, for each mole of $^{117m}$Sn (Sn$^{4+}$) (or total tin) there will be from about one to about three moles of DTPA, either chelated to $^{117m}$Sn (Sn$^{4+}$) or in unchelated form. Preferably, the resulting composition of the invention will contain from about one to about 1.2 moles of DTPA for each mole of $^{117m}$Sn (Sn$^{4+}$).

Figure 2:
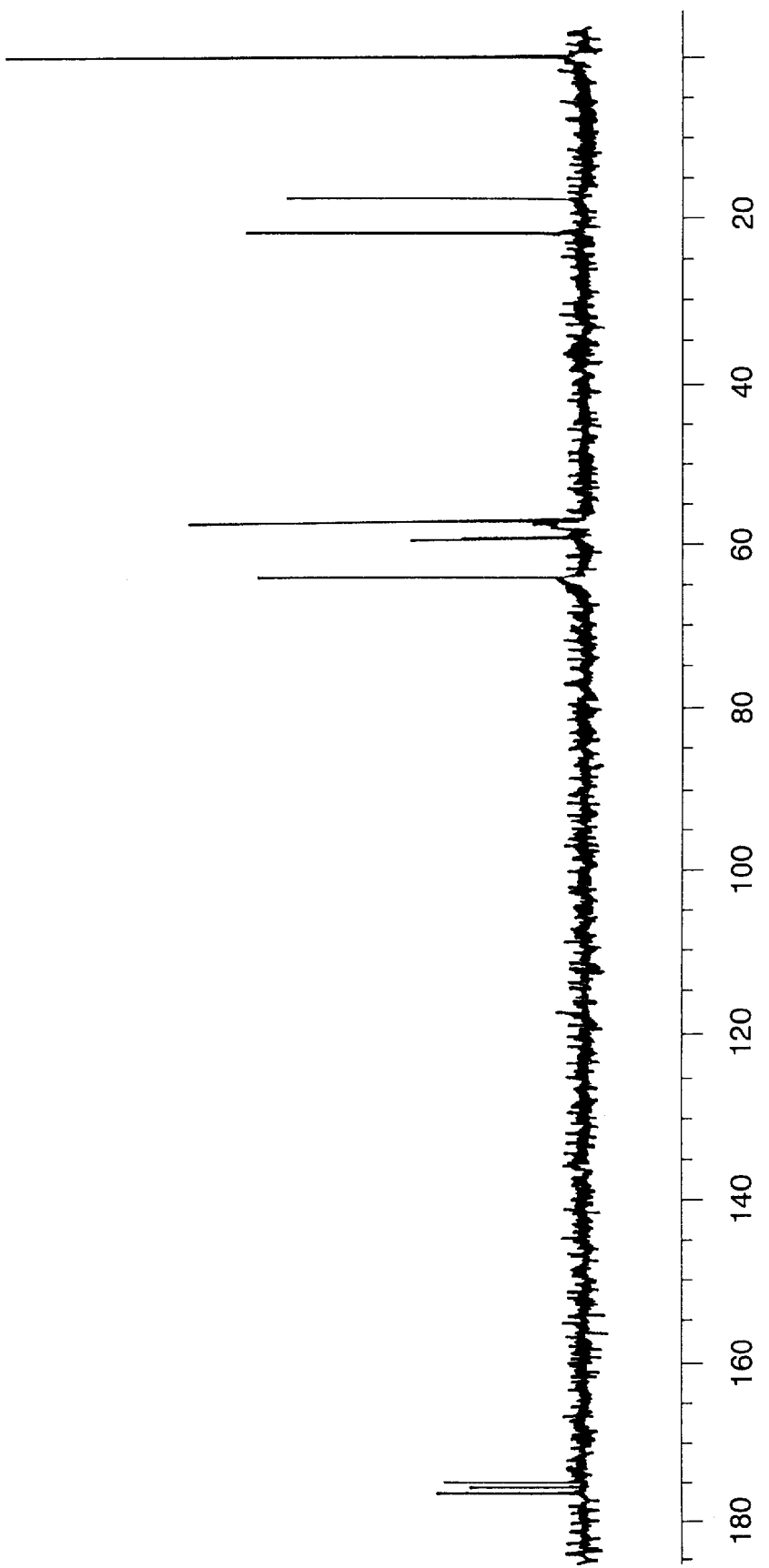
FIG. 2 depicts the analysis of the composition of the invention by $^{13}$C NMR.

The structure of the resulting $^{117m}$Sn(Sn$^{4+}$) DTPA was analyzed by x-ray crystallography, shown in FIG. 1, and $^{13}$C NMR, shown in FIG. 2.

The process of the invention may optionally include the addition of an isotonic vehicle such as Sodium Chloride Injection, Ringer's Injection, Dextrose Injection, Dextrose and Sodium Chloride Injection, Lactated Ringer's Injection, or other vehicle as known in the art. The process can also include the addition of stabilizers, preservatives, buffers, or other additives known to those of skill in the art.

A pharmaceutical composition is also provided that is manufactured by the process described above. The simplified pharmaceutical composition thus produced exhibits substantially the same chemical and biological properties over the composition having a 20:1 ratio of DTPA: Sn(Sn$^{4+}$) prepared by previously known methods.

A method of treating a primary or metastatic tumor in skeletal bone in a mammal is also provided. The method comprises the step of administering a therapeutically effective amount of the pharmaceutical composition as described above.

As defined herein, a therapeutically effective amount means the total amount of each active component of the pharmaceutical composition that is sufficient to show a meaningful patient benefit, i.e., a reduction in the size of the primary or metastatic tumor or in the incidence of additional metastatic tumors. It is contemplated that the administered dosage of the pharmaceutical composition for treatment of osseous tumors will be from about 10 mCi $^{117m}$Sn (Sn$^{4+}$) to about 1000 mCi $^{117m}$Sn (Sn$^{4+}$) per 70 kg body weight (i.e., a total dosage from about 7 mCi to about 1600 mCi). Preferably, the administered dosage is from about 10 mCi $^{117m}$Sn (Sn$^{4+}$) to about 300 mCi $^{117m}$Sn (Sn$^{4+}$) per 70 kg body weight (a total dosage from about 7 mCi to about 500 mCi). More preferably, the administered dosage is from about 10 mCi $^{117m}$Sn (Sn$^{4+}$) to about 100 mCi $^{117m}$Sn (Sn$^{4+}$) per 70 kg body weight (a total dosage from about 7 mCi to about 150 mCi). Most preferably, the administered dosage is from about 12 mCi $^{117m}$Sn (Sn$^{4+}$) to about 25 mCi $^{117m}$Sn (Sn$^{4+}$) per 70 kg body weight (a total dosage from about 9 mCi to about 50 mCi). Ultimately, specific treatment regimens appropriate for individual patients will be determined by the attending physician, taking into account the nature and severity of the condition being treated, and the nature of the prior treatments which the patient has undergone.

A method of treating bone pain associated with cancer in a mammal is also provided. The method includes the step of administering a bone pain palliating amount of a pharmaceutical composition as described above to the mammal.

As defined herein, a "bone pain palliating amount" means the amount of $^{117m}$Sn (Sn$^{4+}$) DTPA sufficient to show a meaningful reduction in bone pain as determined by objective means, for example, using the Keele pain scale (Keele, K. D. (1948) Lancet 2, 6–8) or the Karnofsky performance scale (Karnofsky, D. A. (1963) Clin. Pharmacol. Ther., 709–712). It is contemplated that the administered dosage of the pharmaceutical composition for relief of bone pain will be from about 6 mCi $^{117m}$Sn (Sn$^{4+}$) to about 50 mCi $^{117m}$Sn (Sn$^{4+}$) per 70 kg body weight (i.e., a total dosage from about 4 mCi to about 130 mCi). Preferably, the administered dosage is from about 10 mCi $^{117m}$Sn (Sn$^{4+}$) to about 50 mCi $^{117m}$Sn (Sn$^{4+}$) per 70 kg body weight (a total dosage from about 7 mCi to about 130 mCi). More preferably, the administered dosage is from about 10 mCi $^{117m}$Sn (Sn$^{4+}$) to about 30 mCi $^{117m}$Sn (Sn$^{4+}$) per 70 kg body weight (a total dosage from about 7 mCi to about 80 mCi). Most preferably, the administered dosage is from about 12 mCi $^{117m}$Sn (Sn$^{4+}$) to about 25 mCi $^{117m}$Sn (Sn$^{4+}$) per 70 kg body weight (a total dosage from about 9 mCi to about 65 mCi). Ultimately, specific treatment regimens appropriate for individual patients will be determined by the attending physician, taking into account the nature and severity of the condition being treated, and the nature of the prior treatments which the patient has undergone.

The host or patient for the pharmaceutical composition generally is mammalian. Mammals include, for example, humans, baboons and other primates, as well as pet animals such as dogs and cats, laboratory animals such as rats and mice, and farm animals such as horses, sheep, and cows. Humans are preferred.

Administration of the pharmaceutical can be by any pharmaceutically acceptable mode of administration. Parenteral administration is preferred. Parenteral administration includes, for example, intravenous injection.

EXAMPLE 1

This example demonstrates the simplified synthesis of 1:1.2 $^{117m}$Sn(Sn$^{4+}$) DTPA composition.

Metallic $^{117}$Sn or $^{117m}$Sn (0.10 mmol) was dissolved in 10 ml conc. HCl under an Ar or N$_2$ atmosphere. To solid DTPA was added the tin solution in a 1.2 to 1.0 DTPA to tin molar ratio. After the DTPA was dissolved (5 min), water and HCl were removed under vacuum, and then 20 ml CH$_2$Cl$_2$ was added. After overnight reaction (ultrasonic bath), the sample was evacuated to dryness. Complete conversion to $^{117m}$Sn (Sn$^{4+}$) DTPA was assured by H$_2$O$_2$ oxidation. The solid was taken up in 10 ml water, heated at 100° C. for 30 min, cooled, pH adjusted to 4.2, and reheated at 100° C. for 30 min.

Therefore, a simple synthetic method to prepare an approximate 1:1 $^{117m}$Sn(Sn$^{4+}$)DTPA composition has been developed. These results will facilitate mechanistic studies of tissue localization of $^{117m}$SnDTPA and expand its therapeutic usefulness.

EXAMPLE 2

The structure of the composition manufactured as described in Example 1 was determined by x-ray crystallography, and by $^{13}$C NMR in D$_2$O.

For x-ray crystallography analysis, thin plate colorless crystal of HSn(DTPA) 3H$_2$O were grown from double distilled water. A crystal was mounted on a glass fiber using epoxy and x-ray diffraction data were collected at room temperature. Structure solution and refinement were performed using SHELXL program. Reflections were corrected for absorption using psi-scan data.

The crystal structure is shown in FIG. 1. The crystal structure showed an 8-coordinate chelate with three amino and five carboxyl groups bound to the tin atom [H(SnDTPA) 3H$_2$O crystals; orthorhombic system, space group Pbca with cell constants a=14.07(3), b=12.15(3), c=23.15(3), Z=8].

Carbon-13 NMR spectra were recorded on a Bruker 400MHz spectrometer at room temperature. Chemical shifts are relative either to sodium-3-trimethylsily-tetradeuterioproprionate. The solution for NMR measurements were made up in D$_2$O.

The results from the NMR are shown in FIG. 2. $^{13}$C NMR in D$_2$O [178.81(2), 175.87(2), 172.48(1), 64.21(4), 59.23(2), 57.7(1), 57.0(2)] showed that the octadentate structure was preserved in solution as well.

EXAMPLE 3

Biodistribution studies were performed for the composition of the invention having a DTPA/$^{117m}$Sn(Sn$^{4+}$) ratio of 1.2 and the clinical formulation having a ratio of 20 prepared by previously known methods.

$^{117m}$Sn(Sn$^{4+}$)DTPA at the two molar concentration ratios (1:12 and 1:20) were suspended in PBS. 0.2 ml of each sample were injected into the tail vein of 6–8 week old Balb-C mice weighing approximately 25 grams. Five mice were used for each molar concentration ratio. Biodistribution was determined 24 hours after injection. The mice were sacrificed and the organs removed. Radioactivity was determined by a Packard gamma counter. Full body retention was determined for the remaining caucus, minus the samples.

The biodistribution results for the composition manufactured in Example 1 is set forth in Table 1. Results are set forth in percent injected dose per gram of tissue or organ. The results show that the biodistribution of the 1:1.2 chelate manufactured by the simplified method described in Example 1 was essentially the same as that of the 20:1 clinical formulation.

TABLE 1

Biodistribution in Mice of the $^{117m}$Sn DTPA Chelate[1]

| Molar Ratio DTPA:Tin | Blood | Spleen | Liver | Kidney | Muscle | Bone | Whole Body Retention |
|---|---|---|---|---|---|---|---|
| 20:1 (Original) | 0.015 ± 0.003 | 0.091 ± 0.009 | 0.301 ± 0.049 | 0.745 ± 0.073 | 0.097 ± 0.080 | 15.14 ± 1.15 | 43.2 ± 2.7 |
| 1.2:1 (Synthetic) | 0.013 ± 0.003 | 0.087 ± 0.017 | 0.280 ± 0.039 | 0.678 ± 0.077 | 0.060 ± 0.053 | 16.00 ± 2.20 | 39.6 ± 2.6 |

Stability studies were also performed. Biodistribution studies were performed on the composition of the invention after sitting at room temperature for seven days, one month, and up to six months. As with the 20:1 clinical formulation, distribution remained unchanged indicating stability of the composition.

EXAMPLE 4

Clinical studies have shown that the $^{117m}$Sn(Sn$^{4+}$)DTPA composition is an effective agent for palliation of pain caused by bone metastases. This radiopharmaceutical localizes predominantly in the bone where it emits short-range conversion and Auger electrons. Therefore, it delivers a high dose to bone with no substantial toxicity to marrow tissues. The highest concentration of $^{117m}$Sn are found in the vicinity of bone metastases. Accordingly, it is of interest to explore the potential of $^{117m}$Sn(Sn$^{4+}$)DTPA as an agent to sterilize bone metastases. The present study examines the radiotoxicity of composition of the invention when incorporated into cultured mammalian cells.

Chinese hamster V79 cells were suspended in culture medium containing various concentrations of $^{117m}$Sn(Sn$^{4+}$) DTPA for 14 h and then washed free of all extracellular radioactivity. The cells were then resuspended in fresh culture medium and maintained at 10.5° C. on a rocker-roller for 72 h. Cells were then washed again, serially diluted, and seeded into culture dishes. After 1 week the colonies were stained and counted, the surviving fraction compared to unlabeled controls was determined.

Cellular uptake of $^{117m}$Sn was linearly dependent on the extracellular concentration of $^{117m}$Sn(Sn$^{4+}$)DTPA. The intracellular activity increased linearly in time during the labeling period, remained constant during the 72 h at 10.5° C., and decreased exponentially with an effective half-life of 12.3 h during the colony-forming period. When the survival fraction was plotted as a function of cellular uptake of radioactivity, an exponential response reminiscent of high-LET type radiation emerged. The cellular uptake required to achieve 37% survival was 0.95 mBq/cell. Cellular dosimetry calculations indicate that this corresponds to a mean lethal dose $D_{37}$ of 0.76 Gy. Past studies under identical conditions showed that the survival curve for the energetic beta particle emitter P-32 (orthophosphate) was shouldered (low-LET) with a $D_{37}$ of 7.1 Gy. Therefore, the relative biological effectiveness of $^{117m}$Sn(Sn$^{4+}$)DTPA compared to P-32 orthophosphate is 9.3 in these controlled experiments, but can be expected to be as much as 20 or more in the final clinical application, depending upon the tumor burden of the patient.

The marrow-sparing properties and high-LET type cell killing afforded by the $^{117m}$(Sn$^{4+}$)DTPA of the invention make this radiopharmaceutical an attractive prospect for sterilizing micrometastases in bone.

What is claimed is:

1. A method of making a pharmaceutical composition of $^{117m}$Sn(Sn$^{4+}$) DTPA comprising the steps:

a) dissolving metallic $^{117}$Sn in a concentrated acid suspended in an aqueous medium to form a $^{117m}$SnCl$_2$ solution;

b) adding DTPA to the $^{117m}$SnCl$_2$ solution in a molar concentration ratio of between about 1.0 to about 3.0 DTPA to $^{117m}$SnCl$_2$;

c) allowing the $^{117m}$SnCl$_2$ to react with the DTPA to form a $^{117m}$Sn(Sn$^{2+}$)DTPA complex;

d) oxidizing the $^{117m}$(Sn$^{2+}$)DTPA to form a composition comprising $^{117m}$Sn(Sn$^{4+}$)DTPA; and e) removing the concentrated acid and water from the solution to form to form a resulting solid composition comprising $^{117m}$ Sn(Sn$^{4+}$)DTPA complex with a molar ratio of DTPA to $^{117m}$ Sn(Sn$^{4+}$) of about 1.0 to about 3.0.

2. A method according to claim 1 wherein said concentrated acid is hydrochloric acid.

3. A method according to claim 1 wherein the $^{117m}$Sn has a specific activity from about 0.1 mCi/mg to about 80 Ci/mg.

4. A method according to claim 1 wherein the $^{117m}$Sn has a specific activity from about 2 mCi/mg to about 80 Ci/mg.

5. A method according to claim 1 wherein the $^{117m}$Sn has a specific activity from about 2 mCi/mg to about 20 mCi/mg.

6. A method according to claim 1 wherein the DTPA is added to the solution of $^{117m}$SnCl$_2$ in a molar concentration of between about 1.0 to about 1.2 DTPA to $^{117m}$SnCl$_2$.

7. A method according to claim 1 wherein the resulting solid composition comprises $^{117m}$Sn(Sn$^{4+}$)DTPA with a molar ratio of DTPA to $^{117m}$Sn(Sn$^{4+}$) of about 1.0 to about 1.2.

8. A method according to claim 1 wherein the acid and water are removed under vacuum.

9. A method according to claim 1 wherein said oxidizing step is performed by adding H$_2$O$_2$.

10. A method according to claim 1 wherein said oxidizing step is performed by exposing to open air.

11. A method of making a pharmaceutical composition of $^{117m}$Sn(Sn$^{4+}$) DTPA comprising the steps:

a) dissolving metallic $^{117}$Sn in a concentrated acid suspended in an aqueous medium to form a $^{117m}$SnCl$_2$ solution under an inert atmosphere;

b) adding DTPA to the $^{117m}$SnCl$_2$ solution in a molar concentration ratio of between about 1.0 to about 3.0 DTPA to $^{117m}$SnCl$_2$ in an inert atmosphere;

c) removing the concentrated acid and water from the solution to form a solid residue comprising unchelated $^{117m}$SnCl$_2$ and DTPA;

d) dissolving the solid residue in an organic solvent to form an organic mixture;

e) allowing the organic mixture to react sufficient to allow the formation of a $^{117m}$Sn(Sn$^{2+}$)DTPA complex;

f) oxidizing the $^{117m}$Sn(Sn$^{2+}$)DTPA to form a resulting composition comprising $^{117m}$Sn(Sn$^{4+}$)DTPA with a molar ratio of DTPA to $^{117m}$Sn(Sn$^{4+}$) of about 1.0 to about 3.0.

12. A method according to claim 11 wherein said concentrated acid is hydrochloric acid.

13. A method according to claim 11 wherein the $^{117m}$Sn has a specific activity from about 0.1 mCi/mg to about 80 Ci/mg.

14. A method according to claim 11 wherein the $^{117m}$Sn has a specific activity from about 2 mCi/mg to about 80 Ci/mg.

15. A method according to claim 11 wherein the $^{117m}$Sn has a specific activity from about 2 mCi/mg to about 20 mCi/mg.

16. A method according to claim 11 wherein said inert atmosphere is Ar or $N_2$.

17. A method according to claim 11 wherein the DTPA is added to the solution of $^{117m}$SnCl$_2$ in a molar concentration ratio of between about 1.0 to about 1.2 DTPA to $^{117m}$SnCl$_2$.

18. A method according to claim 11 wherein the resulting composition comprises $^{117m}$Sn(Sn$^{4+}$)DTPA with a molar ratio of DTPA to $^{117m}$Sn(Sn$^{4+}$) of about 1.0 to about 1.2.

19. A method according to claim 11 wherein the acid and water are removed under vacuum.

20. A method according to claim 11 wherein the organic solvent is selected from the group consisting of methylene chloride or ethanol.

21. A method according to claim 20 wherein said organic solvent is methylene chloride.

22. A method according to claim 20 wherein said organic solvent is ethanol.

23. A method according to claim 11 wherein said organic mixture is allowed react from about 8 to about 24 hours.

24. A method according to claim 11 wherein said oxidizing step is performed adding $H_2O_2$.

25. A method according to claim 11 wherein said oxidizing step is performed by exposing to open air.

* * * * *